US00PP18008P2

(12) United States Plant Patent
Jandrew

(10) Patent No.: US PP18,008 P2
(45) Date of Patent: Sep. 11, 2007

(54) ***SCAEVOLA* PLANT NAMED 'BOMY LITBULE'**

(50) Latin Name: *Scaevola aemula*
Varietal Denomination: Bomy Litbule

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/386,621

(22) Filed: Mar. 22, 2006

(51) Int. Cl.
*A01H 5/00* (2006.01)

(52) U.S. Cl. ..... Plt./363

(58) Field of Classification Search ..... Plt./363
See application file for complete search history.

*Primary Examiner*—Kent Bell
(74) *Attorney, Agent, or Firm*—Jondle & Associates P.C.

(57) ABSTRACT

A *Scaevola* plant particularly distinguished by large light blue flowers with small yellow-white eyes, a mid-season and continuous flowering response, medium green foliage with spatulate to elliptical leaves and reddish stems, a vigorous growth habit with a medium to tall plant habit, a decumbent to trailing plant habit, a rounded, well-branched and tight plant habit, and good heat tolerance, is disclosed.

2 Drawing Sheets

Genus and species: *Scaevola aemula.*
Variety denomination: 'Bomy Litbule'.

BACKGROUND OF THE NEW PLANT

The present invention comprises a new and distinct cultivar of *Scaevola,* botanically known as *Scaevola aemula* and hereinafter referred to by the cultivar name 'Bomy Litbule'. The new cultivar originated from a hybridization made in July 2003 in Gilroy, Calif. The female parent was '1012', a proprietary violet-flowered *Scaevola* plant (unpatented), while the male parent was '1035', a proprietary violet-blue-flowered *Scaevola* plant (unpatented).

The new cultivar was created in July 2003 in Gilroy, Calif. and has been asexually reproduced repeatedly by vegetative cuttings and tissue culture in Gilroy, Calif. and Hillscheid, Germany over a one and one-half-year period. The plant has also been trialed at Gilroy, Calif. and Hillscheid, Germany. The present invention has been found to retain its distinctive characteristics through successive asexual propagations.

Plant Breeder's Rights for this cultivar have been applied for in Canada on Jul. 19, 2005.

SUMMARY OF THE INVENTION

The following are the most outstanding and distinguishing characteristics of the new cultivar when grown under normal horticultural practices in Gilroy, Calif. and Hillscheid, Germany.

1. Large light blue flowers with small yellow-white eyes;
2. A mid-season and continuous flowering response;
3. Medium green foliage with spatulate to elliptical leaves and reddish stems;
4. A vigorous growth habit with a medium to tall plant habit;
5. A decumbent to trailing plant habit;
6. A rounded, well-branched and tight plant habit; and
7. Good heat tolerance.

DESCRIPTION OF THE PHOTOGRAPHS

This new *Scaevola* plant is illustrated by the accompanying photographs which show overall plant habit including inflorescences, buds and foliage of the plant; the colors shown are as true as can be reasonably obtained by conventional photographic procedures. The photos are of a 26-week-old plant grown in a greenhouse in an early September trial setting.

DESCRIPTION OF THE NEW CULTIVAR

Figure 1:
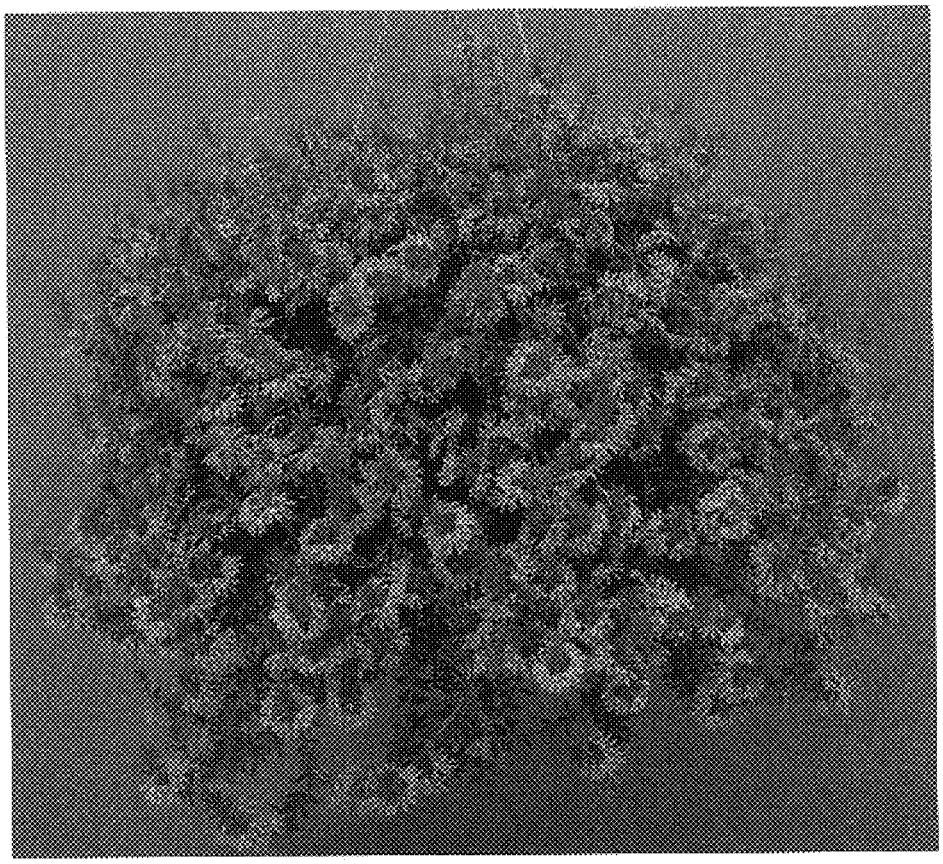
FIG. 1 shows the overall plant habit in a hanging basket, including blooms, buds and foliage.
Figure 2:
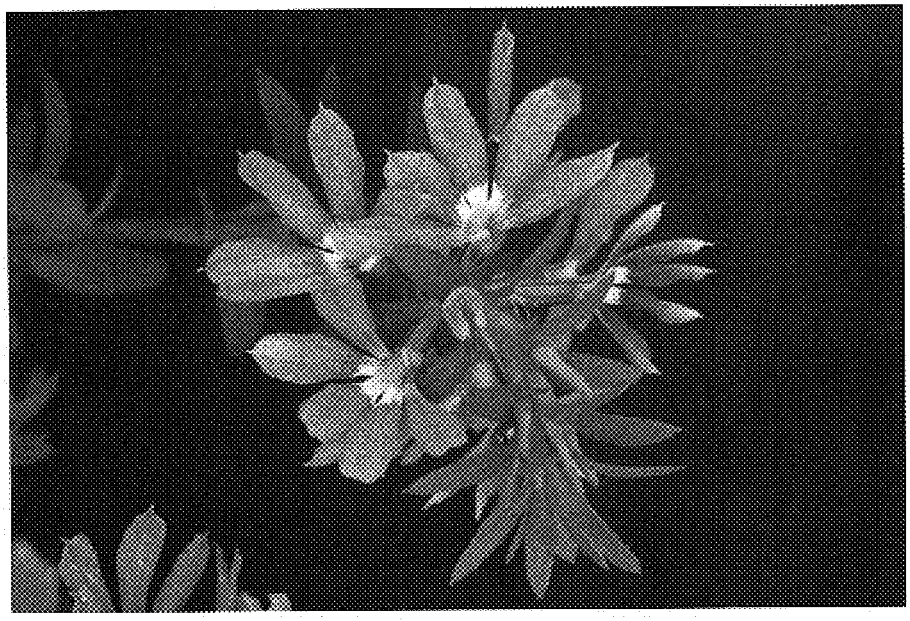
FIG. 2 shows a close-up of the mature inflorescences.

The following detailed descriptions set forth the distinctive characteristics of 'Bomy Litbule'. The data which define these characteristics were collected from asexual reproductions carried out in Hillscheid, Germany. Rooted cuttings were planted into 12-cm plastic pots in early March and pinched once. In late May, the plants were transplanted to outdoor hanging baskets that were situated under light rain protection. The plant history was taken on 11-week-old plants grown in a greenhouse in the Spring and on 26-week-old plants grown outdoors in Hillscheid, Germany in early September 2005. Observations were made in mid-May 2005, when the plants began flowering, and then in mid-August 2005, when the plants were in full-flower. Color readings were taken under natural light. Color references are primarily to The R.H.S. Colour Chart of The Royal Horticultural Society of London (R.H.S.) (2001 edition).

DETAILED BOTANICAL DESCRIPTION

Classification:
*Family.*—Goodeniaceae.
*Botanical.*—*Scaevola aemula.*
*Common name.*—Fan flower.

Parentage:

*Female parent.*—'1012', a proprietary (unpatented) violet-flowered *Scaevola* plant.

*Male parent.*—'1035', a proprietary (unpatented) violet-blue-flowered *Scaevola* plant.

Growth:

*Form.*—Herbaceous perennial.

*Growth and branching habit.*—Initially spreading and later decumbent to trailing; pinching enhances formation of the branches.

*Height* (*measured from the top of the soil*).—8.5 cm for an 11-week-old plant.

*Width* (*horizontal plant diameter*).—26 cm for an 11 -week-old plant.

*Plant spread from the base to the shoot tips, including the flowers*).—82.5 cm for a 26 -week-old plant.

*Time to produce a finished flowering plant.*—12 to 13 weeks for a 12- cm pot in the Spring.

*Outdoor plant performance.*—Use in containers and hanging baskets.

*Time to initiate and develop roots.*—About 25 days.

*Root description.*—Fibrous and self-branching.

Stems:

*Number of branches per plant.*—9 to 12.

*Length.*—10 cm to 14 cm for a 11-week-old plant.

*Diameter* (*measured from the midpoint*).—0.3 cm.

*Internode length.*—3 cm to 6 cm.

*Color.*—RHS 137C with RHS 181A to RHS 181B anthocyanin on the upper ends.

*Texture.*—Glabrous.

Leaves:

*Arrangement.*—Alternate.

*Immature leaf.*—Color: Upper surface: RHS 137B (medium green) with RHS N77B anthocyanin near the margins. Lower surface: Between RHS 137D and RHS 143A.

*Mature leaf.*—Color: Upper surface: RHS 137B (medium green). Lower surface: Between RHS 137D and RHS 143A. Length: Up to 6.0 cm for young plants and about 3.5 cm for flowering branches. Width: 2.5 cm for non-flowering stems and 1.1 cm to 1.3 cm for flowering stems. Shape: Initially spatulate and later elliptic. Apex: Obtuse to acute. Base: Attenuate. Margin: Initially distinctly dentate and later only a few weak lobes. Texture: Pilose. Venation: Midrib is longitudinal and protrudes on the lower surface; other veins are indistinct elsewhere. Venation color: RHS 144A for the lower surface.

*Petioles.*—Not clearly distinct from the base of the leaf.

Flower buds:

*Shape.*—Elongated and slightly conical.

*Length.*—2.2 cm.

*Diameter.*—Up to 0.4 cm.

*Color* (*at tight bud*).—RHS N77C (grayish-purple) with RHS 145A (light green) tips.

Inflorescence:

*Blooming habit.*—Continuously from the Spring through the Fall; flowers appear about 12 to 13 weeks after planting rooted cuttings.

*Lastingness of individual blooms on the plant.*—About one week.

*Fragrance.*—None.

*Inflorescence type.*—Solitary flowers arise from the leaf axial with one flower per leaf axil in an alternate arrangement; 5 to 9 open flowers at any time.

*Flower type.*—Composed of 5 petals slanting upward and fused at the base and in a fan-like arrangement to form a lower part which is open tube-shaped.

*Pedicels.*—None, flowers are sessile.

Flowers:

*Flower diameter.*—Up to 3.1 cm.

*Flower depth.*—2.7 cm.

*Flower tube.*—Shape: Open tube. Tube length: 1.6 cm. Tube diameter (at the opening): 0.5 cm.

*Petals.*—Shape: Cuspidate (mainly rounded but with a tiny pointed tip). Apex: Acuminate or cuspidate. Base: Fused. Margin: Entire. Texture: Smooth. Color: Immature: Upper surface: RHS N87C. Lower surface: RHS N88C. Mature: Upper surface: RHS N87C to RHS N87D with traces of an RHS N80B (purple) mid-line. Lower surface: RHS N88D with narrow and weak RHS 177D (brown) stripes.

*Throat color.*—Inner surface: RHS 12A (yellow) and RHS 175A stripes along the margins. Outer surface: RHS 150C (greenish-yellow) and weak RHS 175A stripes along the margins.

*Sepals.*—General: Composed of one larger and somewhat fleshy sepal and two narrow sepals at the base of the flower. Shape: Lanceolate for the larger sepal and ligulate for the two narrow sepals. Apex: Acute. Base: Sessile. Margin: Entire. Texture: Sparsely pubescent. Color: RHS 143A for both the upper and lower surfaces. Length: 1.1 cm. Width: Up to 0.4 cm for the large sepal and 0.1 cm for the narrow sepals.

Reproductive organs:

*Stamen.*—Quantity: 5, protruding from the flower throat. Anther shape: Narrow, ovate. Anther length: 0.3 cm. Anther color: RHS 151A (yellowish). Filament color: RHS 150D (whitish). Filament diameter: 0.1 cm. Filament length: 0.3 cm. Pollen amount: Sparse. Pollen color: RHS 4D (yellow-white).

*Pistils.*—Quantity: 1. Pistil length: 1.5 cm. Style diameter: 0.4 cm at the tip. Style color: RHS 183B. Stigma color: RHS 150D (whitish).

Fruit/seed set: None observed.

Disease and insect resistance: No special observations made.

COMPARISON WITH PARENTAL AND COMMERCIAL CULTIVARS

'Bomy Litbule' differs from the female parent '1012' (unpatented), in that 'Bomy Litbule' has larger flowers and a more compact habit than '1012'.

'Bomy Litbule' differs from the male present '1035' (unpatented), in that 'Bomy Litbule' has a lighter blue flower color, an earlier flowering response and a more compact plant habit than '1035'.

'Bomy Litbule' differs from the variety 'Bomy Pinka' (U.S. Plant patent application Ser. No. 11/386,620) primarily in flower color.

'Bomy Litbule' differs from the commercial variety 'Blue Wonder' (U.S. Plant Pat. No. 7,929), in that 'Bomy Litbule' has larger flowers that are a lighter violet-blue hue than 'Blue Wonder'.

'Bomy Litbule' differs from the commercial variety 'Newon' (U.S. Plant Pat. No. 10,584), in that 'Bomy Litbule' has lighter blue flowers, more serrated leaves, and a fuller plant habit (due to a greater number of branches) than 'Newon'.

I claim:

1. A new and distinct cultivar of *Scaevola* plant as shown and described herein.

* * * * *